(12) United States Patent
Ford

(10) Patent No.: US 7,390,297 B2
(45) Date of Patent: Jun. 24, 2008

(54) METHOD AND APPARATUS FOR RELIEVING ERECTILE DYSFUNCTION

(76) Inventor: Jere B. Ford, #606, 1616 16th St., Washington, DC (US) 20009

( * ) Notice: Subject to any disclaimer, the term of this patent is extended or adjusted under 35 U.S.C. 154(b) by 183 days.

(21) Appl. No.: 11/391,763

(22) Filed: Mar. 28, 2006

(65) Prior Publication Data

US 2007/0238919 A1   Oct. 11, 2007

(51) Int. Cl.
*A61F 5/00* (2006.01)
(52) U.S. Cl. ......................................................... 600/41
(58) Field of Classification Search ............. 600/38–41
See application file for complete search history.

(56) References Cited

U.S. PATENT DOCUMENTS

| | | |
|---|---|---|
| 4,139,007 A | 2/1979 | Diamond |
| 4,203,432 A | 5/1980 | Koch |
| 4,220,016 A | 9/1980 | Frenger |
| 4,407,275 A | 10/1983 | Schroeder |
| 4,539,980 A | 9/1985 | Chaney |
| 4,718,411 A | 1/1988 | Stewart |
| 4,834,115 A | 5/1989 | Stewart |
| 4,960,113 A | 10/1990 | Seeberg-Elverfeldt |
| 5,195,943 A | 3/1993 | Chaney |
| 5,683,383 A | 11/1997 | Russell |
| 5,855,548 A | 1/1999 | Place |
| 5,873,813 A | 2/1999 | Weiss |
| 6,036,635 A | 3/2000 | Altshuler |
| 6,162,188 A | 12/2000 | Barnea |
| 6,231,502 B1 | 5/2001 | McCarty |
| 6,251,067 B1 | 6/2001 | Strickholm |
| 6,258,059 B1 | 7/2001 | Weston |
| 6,309,344 B1 | 10/2001 | Werner |
| 6,458,073 B1 | 10/2002 | Bonthuys |
| 6,485,408 B2 | 11/2002 | Orten |
| 6,705,987 B2 | 3/2004 | Anderson |
| 2002/0103415 A1 | 8/2002 | Manska |
| 2003/0009082 A1 | 1/2003 | Yanagi |
| 2004/0094163 A1 | 5/2004 | Benson |
| 2004/0242957 A1 | 12/2004 | Ward |
| 2005/0065159 A1 | 3/2005 | Adams |
| 2005/0277907 A1 | 12/2005 | Jackson |
| 2005/0283044 A1 | 12/2005 | Chang |

OTHER PUBLICATIONS

Jolly Roger Mood Cockring Adult Novelty; Sensual Universe; Nov. 8, 2004; pp. 1-3.*

* cited by examiner

*Primary Examiner*—John P Lacyk
(74) *Attorney, Agent, or Firm*—The H.T. Than Law Group

(57) ABSTRACT

A restrictor for relieving the symptoms of erectile dysfunction by applying pressure to the corpora cavernosa. The restrictor includes a visual gauge for signaling a purchaser of adequate fit and/or potential overuse. The restrictor includes a surface treatment that changes temperature with color. The restrictor may be a rigid metal ring having a thermochromic surface treatment, such as a layer of liquid crystals covered with transparent glass or plastic. The restrictor may also be a flexible band wrapped in or made from a material dyed with a leuco dye or a dye including microencapsulated liquid crystals in suspension. The color change indicated by the thermochromic surface treatment indicates adequate fit and/or potential overuse.

17 Claims, 3 Drawing Sheets

METHOD AND APPARATUS FOR RELIEVING ERECTILE DYSFUNCTION

BACKGROUND

The invention relates generally to devices for safely alleviating erectile dysfunction. In particular, the invention relates to a device secured around the penis to restrict blood flow out of the penis while providing a visual cue for signaling the level of restriction.

Erectile dysfunction (ED) is a medical condition for which millions of American men seek treatment every year. According to the National Institutes of Health, between 15 million and 30 million men suffer from ED, which is loosely defined as the repeated inability to get or keep an erection firm enough for sexual intercourse. The wide range of the estimate of sufferers stems from the rather vague definition, as ED can be a total inability to achieve erection, an inconsistent ability to do so, or a tendency to sustain only brief erections. Under normal conditions, an erection is achieved when blood flows into the penis and fills the corpora cavernosa, large cylindrical tissue structures which run the length of the penis and, when filled with blood, cause the penis to become rigid and erect. The corpora cavernosa are surrounded by the tunicae, elastic sheaths which expand with the corpora cavernosa and apply pressure to the veins which would normally drain the blood from the corpora cavernosa. In some cases, the cause of ED is linked to an inability to provide sufficient blood flow to the penis to fill the corpora cavernosa and achieve an erection. In other situations, the tunicae are not able to press against the blood-draining veins with sufficient force to maintain the erection.

While many of those afflicted with ED are older, with approximately half of the sufferers believed to be over the age of 65, ED is a condition which can affect men at any age, as the causes of ED are extremely varied. Damage to nerves, arteries, smooth muscles, and fibrous tissues from disease is the most common cause of ED. These diseases, such as diabetes, multiple sclerosis, atherosclerosis, and vascular disease, account for about 70 percent of ED cases. In addition, many common medicines including blood pressure drugs, antihistamines, and antidepressants can result in ED. Certain risky lifestyle choices, such as smoking, being overweight, and avoiding exercise, may also contribute to ED. It is also believed that psychological factors, such as stress, anxiety, depression, and fear of sexual failure, cause approximately 10 to 20 percent of ED cases.

Many methods for alleviating ED are known. For example, surgical treatment options exist. However, these surgeries are radical and invasive, as they involve implanting inflatable members into the penis. These members can be inflated by pumping fluid into the members when sexual intercourse is desired. Due to the cost, side effects, and invasive nature of the surgery, the surgical option is not considered viable by many men, especially those who suffer from a more mild form of the condition.

The pharmaceutical industry has also produced many options for ED sufferers. These drug remedies may be pills or liquids taken orally, such as phosphodiesterase inhibitors which increase blood flow to the penis. Viagra®, Levitra®, and Cialis® are popular phosphodiesterase inhibitors. While popular, these drugs are not suitable for many men, including patients also suffering from heart disease. As the majority of ED sufferers are older men who frequently also have heart disease, oral ED drugs may not be suitable for the majority of ED sufferers. Furthermore, even if an ED sufferer is physically capable of taking the oral drugs, they may not wish to do so, as the drugs can take up to one hour to be effective or can cause priapism, a painful and persistent erection caused by over-constriction of the corpora cavernosa-draining veins.

Other drug options include injecting drugs directly into the penis. Drugs such as papaverine hydrochloride, phentolamine, and alprostadil widen blood vessels to allow more blood to flow into the penis. While these erections are achieved nearly instantaneously, these drugs can cause undesirable side effects, including priapism and scarring. Furthermore, many men may be extremely reluctant to insert a needle into the sensitive skin of the penis.

Mechanical devices are also available for producing and/or maintaining erections. These devices include large, cumbersome vacuum pumps for drawing blood into the penis and restrictors which hold blood in the penis by applying pressure to the subcutaneous veins which drain the penis of blood. Especially for those who suffer from the more mild forms of ED, restrictors are a very popular option. Such restrictors include continuous rigid rings, adjustable straps, or the like. Restrictors are described, for example, in U.S. Pat. No. 5,855, 548 (rubber tubing looped around the base of the penis), U.S. Patent Pub. US 2003/0009082 (an adjustable gold ring through which the penis is inserted), U.S. Patent Pub. US 2004/0242957 (an adjustable rigid band encircling a portion of the base of the penis), and U.S. Patent Pub. US 2005/0277907 (joined elastic rings worn around the scrotum and the base of the penis).

While effective in treating ED, especially for mild ED, restrictors also pose certain risks, mostly related to trapping blood within the penis for extended periods of time and over-restricting the vessels of the penis. The Food and Drug Administration has suggested guidelines for using restrictors, also called constriction rings, which include only wearing the restrictor for thirty (30) minutes or less per use, waiting at least an hour between uses, cleaning the restrictor thoroughly between uses, and carefully selecting the properly sized restrictor.

Selecting the properly sized restrictor is extremely critical to effective and safe usage of a restrictor, especially if the restrictor chosen is a rigid continuous ring. If the restrictor is too loose, then the restrictor will not be effective in relieving the symptoms of ED. If the restrictor is too tight, then serious consequences such as permanently damaging the penis, may occur.

Currently, sizing of restrictors is performed by trained personnel, a situation that many in need of restrictors find too embarrassing to endure. As a consequence, many men either deny themselves the restrictors or take the chance that the one they purchase will fit appropriately. Therefore, a need exists for a purchaser of a restrictor to size a restrictor privately. Furthermore, no restrictors currently available include a signal or gauge to let a user know if the restrictor has reached an unsafe level of restriction. Therefore, a need exists for a gauge to signal a user of a restrictor of a potentially hazardous condition.

SUMMARY OF THE INVENTION

An aspect of the invention is directed toward a restrictor for relieving erectile dysfunction including a band and a temperature gauge connected to the band at or near an exterior surface of the band.

Another aspect of the invention is directed toward a method for relieving erectile dysfunction comprising the steps of: (i) providing a restrictor having a temperature gauge attached thereto, wherein the temperature gauge may be interpreted visually while worn, (ii) securing the restrictor around a penis, (iii) monitoring the temperature gauge to determine changes in a skin temperature of the penis, and (iv) adjusting use of the restrictor according to the monitored skin temperature change

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
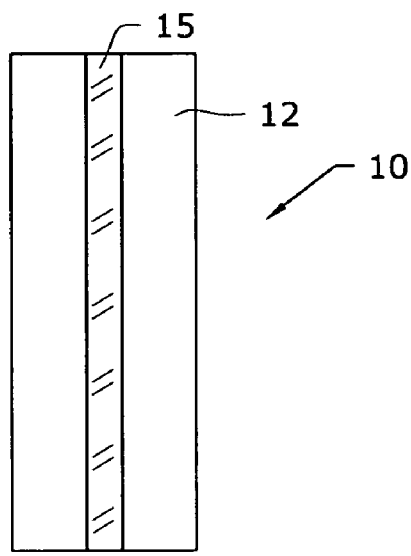
FIG. 1 is a front view of a restrictor having a visual gauge according to the present invention.
Figure 2:
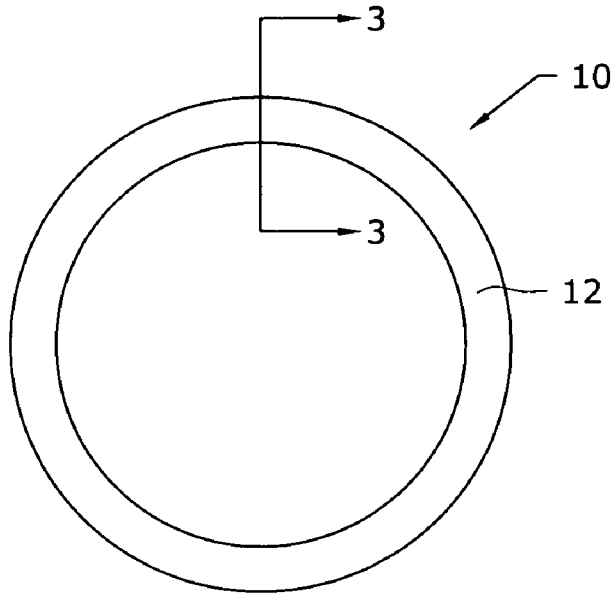
FIG. 2 is a side view of the restrictor of FIG. 1.

As illustrated in the accompanying drawings and discussed in detail below, the present invention is directed toward a restrictor for alleviating the symptoms of erectile dysfunction (ED) while providing a visual cue for sizing or to indicate a potentially hazardous condition. As shown in FIGS. 1 and 2, a restrictor 10 includes a band 12 formed into a continuous ring. Band 12 is preferably formed from a rigid material that readily transfers heat. Any such material known in the art is appropriate for use with the present invention. Examples of materials for band 12 include metals such as steel, titanium, gold, silver, aluminum, chrome, and the like, ceramic materials, plastic, etc. Band 12 may be made using any method known in the art, such as forging, stamping, casting, molding, or the like.

A temperature gauge 15 is applied to band 12, where temperature gauge 15 is preferably set into a channel 13 formed at or near the surface of band 12. It will be recognized by those in the art that channel 13 may extend entirely around band 12 or over just a portion thereof.

While any temperature gauge known in the art is appropriate for use with the present invention, preferably temperature gauge 15 displays the temperature or temperature change so as to be interpreted easily by the user without having to link temperature gauge 15 to an external display. Additionally, temperature gauge 15 is preferably able to be applied with a smooth finish so as not to endanger the user or the user's partner during use of restrictor 10. Preferably, temperature gauge 15 includes a layer 16 of thermochromic material applied to band 12 so that the change in temperature is readily indicated by a color change indicated on the surface of band 12. Appropriate thermochromic materials include liquid crystals, such as cholesteryl nonanoate and cyanobiphenyls, and leuco dyes such as spirolactones, fluorans, spiropyrans, and fulgides. If leuco dyes are used, a suspension of micocapsules is preferably formed, where each microcapsule includes a leuco dye, a weak acid, and a dissociable salt dissolved in a solvent such as dodecanol. Appropriate weak acids include bisphenol A, parabens, and 4-hydroxycoumarin. The operation of these thermochromic materials is discussed in greater detail below.

A cover 14 is affixed over thermochromic layer 16 to provide a smooth finish and to prevent the thermochromic materials from becoming contaminated, leaking, or otherwise damaged. Cover 14 may be made from any transparent or translucent material capable of sealing thermochromic layer 16 while allowing a user to read the visual cues provided by thermochromic layer 16. Such materials include glass, tempered glass, plastics, and the like. If glass, cover 14 may be inserted into channel 13 and glazed to seal thermochromic layer 16 therewithin. If made from a plastic or similar lower-temperature melting point material, cover 14 may be molded directly over thermochromic layer 16 in situ.

In use, a potential purchaser or user inserts the flaccid penis through band 12 and affixes band 12 such that it encircles both the shaft of the penis near the base thereof and the scrotum. Band 12 should fit securely enough that pressure sufficient to cause blood to remain in the penis is applied by restrictor 10. If band 12 is too large, restrictor 10 will not trap sufficient blood within the corpora cavernosa to maintain an erection. If band 12 is too small, restrictor 10 may cause bruising, or, in severe cases, priapism where medical treatment must be sought in order to remove restrictor 10 and relieve the priapism. As blood fills the penis due to the presence of restrictor 10, the surface temperature of the penis will rise. As band 12 rests against the body, band 12 is heated to the skin temperature, which transfers the skin temperature to thermochromic layer 16.

Thermochromic layer 16 may be monitored to determine the temperature of the surface of the penis. As a thermochromic material is used, the user simply monitors the color of thermochromic layer 16. Thermochromic layer 16 is preferably calibrated, such as by adjusting the composition or thickness thereof, so that a mid-range color is set to the average skin temperature of a person, typically between about 80 and 84 degrees Fahrenheit. For example, when thermochromic liquid crystals are heated, the crystalline structure of the liquid crystals changes, widening the spaces between the crystalline layers so that different colors are absorbed and reflected. Many thermochromic liquid crystals display colors ranging from black when "cold" to green at average skin temperature to dark blue when "hot". This technology is well-known, for example, in mood rings. With liquid crystals as thermochromic layer 16, a properly fitted band 12 would result in a color ranging from green to light blue during use. If thermochromic layer 16 registers dark green to black, then restrictor 10 is too large, i.e., insufficient heat is being generated at the skin surface, and a smaller restrictor should be purchased.

The color change may also be monitored so that restrictor 10 is used properly. For example, if restrictor 10 over-restricts the corpora cavernosa or remains on the corpora cavernosa too long, the trapped blood within the corpora cavernosa will eventually cool as a fresh supply of blood cannot maintain the temperature of the blood therewithin. Over time, if thermochromic layer 16 first reflects a rise in temperature but later reflects a decrease in temperature while the penis remains erect, restrictor 10 should be removed.

Leuco dyes typically provide only a single color change, for example from pink to purple or green to yellow, depending upon the leuco dye selected. Leuco dyes change color when exposed to acids in the presence of a dissociable salt. When microencapsulated for use thermochromic layer 16, the leuco dye, a weak acid, and a dissociable salt dissolved in a solid solvent are encapsulated together. The solvent melts at a chosen temperature, allowing the salt to lower the pH of the mixture, thereby protonating the dye. As such, the absorption spectrum of the dye shifts dramatically, resulting in a color change. As such, if a leuco dye suspension is used as thermochromic layer 16, then thermochromic layer 16 could be triggered to change color either proper fit is achieved and when safe usage is exceeded, if a combination of dyes and solvents which melt at different temperatures are used. An instructive color guide may be provided with restrictor 10 for self-interpretation of the color changes.

Figures 4, 5:
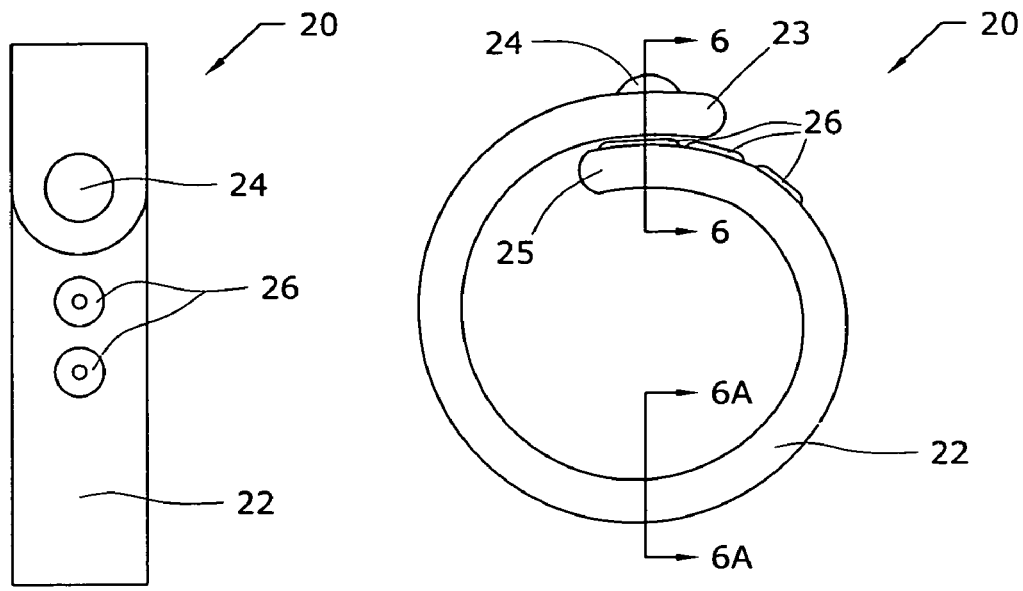
FIG. 4 is a front view of an alternate embodiment of a restrictor having a visual gauge according to the present invention.
FIG. 5 is a side view of the restrictor of FIG. 4.
Figure 6:
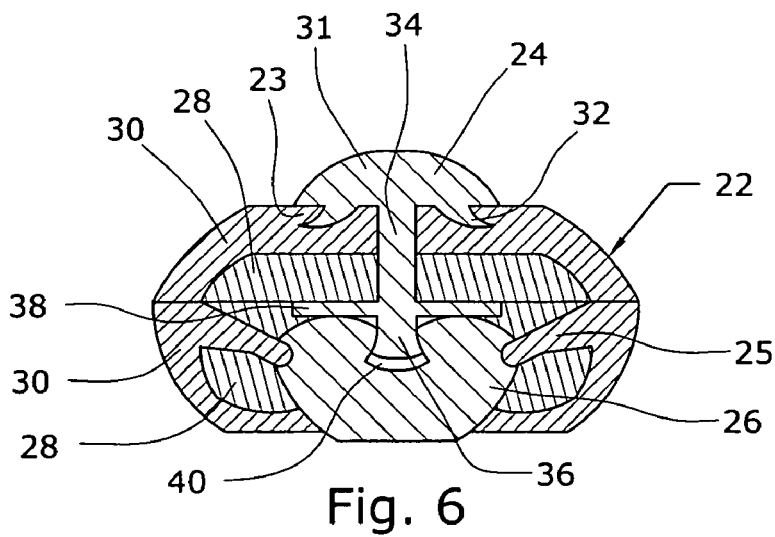
FIG. 6 is a cross-sectional view of the restrictor of FIG. 5 taken along line 6-6 thereof.

FIGS. 4-6 show another embodiment of a restrictor 20 according to the present invention. In this embodiment, restrictor 20 is adjustable, being made of a flexible band 22. Several points of closure, female fasteners 26, are provided so that the fit of restrictor 20 can be readily adjusted, either for proper restriction or for removal.

Figure 6A:
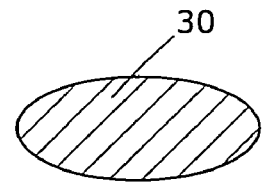
FIG. 6A is an alternate cross-sectional view of the restrictor of FIG. 5 taken along line 6A-6A thereof.

As seen in FIG. 6, flexible band 22 includes two layers: a main strap material 28 and a temperature gauge material 30. Main strap material 28 may be material known in the art, such as cloth, leather, vinyl, rubber, silicone, thin or linked metal, or the like. Temperature gauge material 30 is a natural or synthetic woven or non-woven cloth impregnated with microencapsulated leuco dyes, as described above with respect to the first embodiment. Temperature gauge material 30 is preferably permanently affixed to main strap material, such as with an adhesive, stitching, or by any other method known in the art. FIG. 6A shows an alternate cross-section, where band 22 is made of a single layer of temperature gauge material 30.

Flexible band 22 is formed into a circle by joining the two ends thereof, such as with the snap closure shown in FIG. 6. A first end 23 includes a male fastener 24 which is configured to be joined to one of several female fasteners 26 disposed on a second end 25 of flexible band 22. Alternatively, first end 23 may include a single female fastener 26 while a plurality of male fasteners 24 are disposed on second end 25 of flexible band 22. For example, male fastener 24 pierces through first end 23 of band 22 such that a top portion 31 grips the outside surface of band 22 with grips 32. A post 34 extends through band 22 and terminates in a ball 36. Ball 36 preferably has a slightly larger diameter than post 34. A stabilizing plate 38 anchors post 24 to the underside of band 22. Female fastener 26 is affixed to second end 25 of band 22 by piercing through and capturing a portion of band 22 within a portion of female fastener 26. Female fastener includes an indentation 40, which is sized to receive ball 36 and post 34 by press fitting. When pushed together, female fastener 26 retains post 34 and ball 36 of male fastener 24 within indentation 40 until removed. It will be apparent to those in the art that any type of fastener is appropriate for use with restrictor 20, such as a buckle, buttons, a double-D ring cinch, and the like. It will also be apparent to those of skill in the art that an elastic material may be used for main band material 28, making any closures unnecessary. In other words, flexible band 22 can form a continuous circle that can stretch when necessary for insertion or removal.

When restrictor 20 is fitted properly around the base of the penis and scrotum, temperature gauge material 30 absorbs heat from the skin and responds to the skin temperature with a first color change. If restrictor 20 is too loose, no color change happens, and restrictor 20 should be tightened. If a second color change of temperature gauge material 30 occurs, e.g., temperature gauge material 30 reverts back to its original color and the penis is still erect, then restrictor 20 is too tight or has been worn too long and should be promptly removed.

Figures 7, 7A:
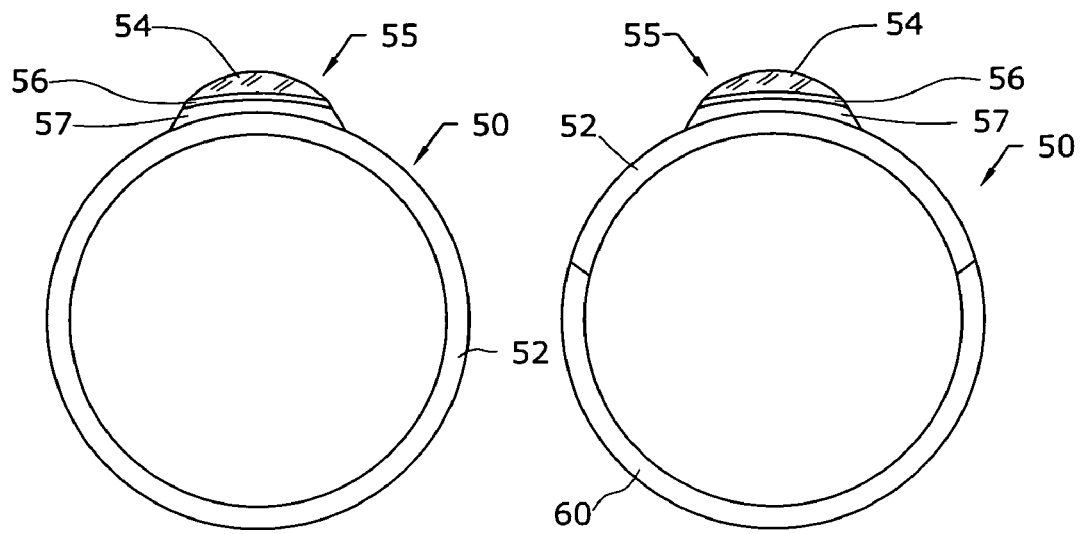
FIG. 7 is a front view of another alternate embodiment of a restrictor having a visual gauge according to the present invention.
FIG. 7A is a front view of the restrictor shown in FIG. 7 including an elastic portion.
Figure 8:
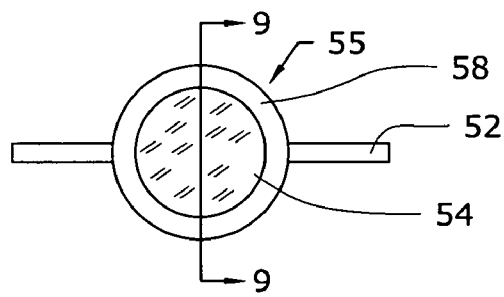
FIG. 8 is a side view of the restrictor of FIG. 7.
Figure 9:
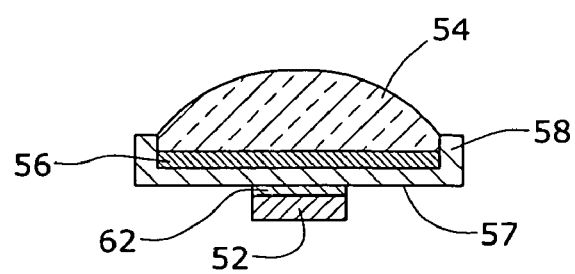
FIG. 9 is a cross-sectional view of the restrictor of FIG. 8 taken along line 9-9 thereof.

A third restrictor 50 according to the present invention is shown in FIGS. 7-9. In this embodiment, a band 52 forms at least a portion of restrictor 50. Band 52 is similar to band 12 discussed above, in that band 52 is formed of a rigid material that readily transfers heat, such as metal. As shown in FIG. 7, band 52 may form the entirety of restrictor 50. Alternatively, as shown in FIG. 7A, band 52 may form just a portion of restrictor 50, with a flexible material 60 forming the remainder thereof and attached to band 52 by any means known in the art, such as with an adhesive, sewing, or the like. Flexible material 60 may be elastic, in which case flexible material 60 and band 52 form a continuous loop, or flexible material 60 may be inelastic, in which case a connector such as shown and discussed above may be used.

Affixed to a surface of metal band 52 is at least one temperature gauge 55. Temperature gauge 55 preferably reflects temperature changes via color change, as discussed above. Temperature gauge 55 includes a base 57, a thermochromic layer 56 and a cover 54. As shown in FIG. 9, temperature gauge 55 is preferably secured to band 52 at base 57 with a layer 62 of solder or similar material. Alternatively, base 57 may be affixed to a flexible material, such as by wrapping tabs around the flexible material where the tabes are capable of transferring heat quickly to base 57. However, temperature gauge 55 may be secured to base 52 by any means known in the art, such as with an adhesive or by welding. However, layer 62 should be selected so as not to inhibit the heat transfer from band 52 to base 57.

Figure 3:
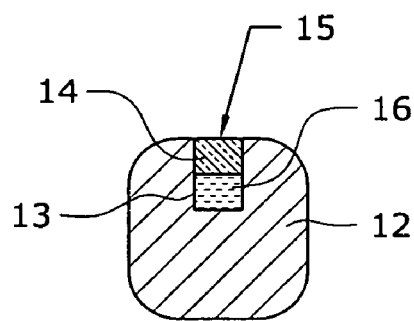
FIG. 3 is a cross-sectional view of the restrictor of FIG. 1.

Thermochromic layer 56 may be a layer of liquid crystals or a suspension of leuco dyes, as discussed above with respect to FIGS. 1-3. The thickness of thermochromic layer 56 may be selected to determine the rate and extent of the color change; a thinner layer 56 will reach the skin temperature more quickly and change colors rapidly, while a thicker layer 56 will do so more slowly. It will be recognized by those in the art that thermochromic layer 56 may also substantially fill a cavity (not shown) formed within cover 54.

Cover 54, similar to cover 14 described above, is a transparent or translucent material which seals thermochromic layer 56 to base 57. Cover 54 may be made from glass, plastic, or the like. Although shown in FIG. 9 to provide a dome-like shape to temperature gauge 55, cover 54 may have any configuration desired, provided that the color changes of thermochromic layer 56 may still be readily observed by a user therethrough. Cover 54 may be secured to thermochromic layer 56 and/or base 57 by any means known in the art, such as with an adhesive, by glazing, or by pressing a portion of base 57 over cover 54 to secure cover 54 to base 57.

Base 57 may be made from any material known in the art capable of readily transferring heat from band 52 to thermochromic layer 56. For example, base 57 may be made from metals, such as steel, titanium, aluminum, gold, and silver, ceramics, polymers, or the like. Preferably base 57 is made form a rigid material capable of providing structural support for thermochromic layer 56 and cover 54. Base 57 may have any shape known in the art, such as circular, elliptical, ovoid, or polygonal. Base 57 preferably includes a rim portion 58 which forms sidewalls that extend at least over thermochromic layer 56 to provide additional protection.

Restrictor 50 is worn at the base of the penis and around the scrotum as discussed above. When restrictor 50 is worn, skin temperature heats band 52. This heat is transferred from band 52 to thermochromic layer 56 via base 57. When sufficient heat is transferred to thermochromic layer 56, thermochromic layer 56 begins to change color. The color change can them be interpreted by the user, for example by comparing the color of temperature gauge 55 to a chart provided by the manufacturer, to determine if the fit is correct and/or if restrictor 50 is being used safely.

While it is apparent that the illustrative embodiments of the invention disclosed herein fulfill the objectives of the present invention, it is appreciated that numerous modifications and other embodiments may be devised by those skilled in the art. Additionally, feature(s) and/or element(s) from any embodiment may be used singly or in combination with feature(s) and/or element(s) from other embodiment(s). Therefore, it will be understood that the appended claims are intended to cover all such modifications and embodiments, which would come within the spirit and scope of the present invention. All publications discussed herein, including but not limited to patents, patent applications, articles, and books, are incorporated by reference in their entireties.

The invention claimed is:

1. A restrictor for relieving erectile dysfunction comprising:
    a band configured to compress the corpora cavernosa; and
    a temperature gauge connected to the band at or near an exterior surface of the band, wherein the temperature gauge comprises a thermoebromic material, wherein at least a portion of the band forms a continuous loop, and further comprising a channel formed at or near a surface of the band, wherein the channel is configured to receive the thermochromic material.

2. A restrictor for relieving erectile dysfunction comprising:
    a band configured to compress the corpora cavernosa; and
    a temperature gauge connected to the band at or near an exterior surface of the band, wherein the temperature gauge comprises a thermoebromic material, wherein at least a portion of the band forms a continuous loop, wherein the themochromic layer is disposed between a base and a cover, and wherein the base is affixed to the band.

3. The restrictor of claim 2, wherein the base is affixed to the band by a layer, wherein the layer comprises an adhesive, solder, or welding filler material.

4. The restrictor of claim 1, wherein the band is formed from a first material and a second material, wherein the first material is more rigid than the second material.

5. The restrictor of claim 2, wherein the band is formed from a first material, wherein the first material is attached to a second material that is more flexible than the first material.

6. The restrictor of claim 4, wherein the second material of the band comprises elastic material.

7. The restrictor of claim 5, wherein the second material of the band comprises an elastic material.

8. The restrietor of claim 6, wherein the band is adjustable.

9. The A restrictor for relieving erectile dysfunction comprising:
    a band configured to compress the corpora cavernosa; and
    a temperature gauge connected to the band at or near an exterior surface of the band, wherein the temperature gauge comprises a thermochromic material, wherein the two ends of the band are connected to form a loop, wherein the temperature gauge comprises a cloth impregnated with a leuco dye.

10. The restrictor of claim 9, wherein at least a portion of the band comprises the temperature gauge.

11. The A restrictor for relieving erectile dysfunction comprising:
    a band configured to compress the corpora cavernosa; and
    a temperature gauge connected to the band at or near an exterior surface of the band, wherein the temperature gauge compnses a thermochromic material, wherein the two ends of band are connected to form a loop, wherein the temperature gauge comprises a base, a cover attached to the base, and a layer of thermochromic material disposed between the base and the cover, wherein the base is connected to the band.

12. A method for relieving ercetile dysfunction comprising the steps of:
    (i) providing a restrictor having a temperature gauge attached thereto, wherein the temperature gauge is interpreted visually while worn,
    (ii) securing the restrictor around at least a portion of a penis;
    (iii) monitoring the temperature gauge to determine changes in a skin temperature of the penis; and
    (iv) adjusting use of the restrictor according to the monitored skin temperature change.

13. The method of claim 12, wherein the temperature gauge comprises a themochromic material, and wherein the temperature gauge is monitored in step (iii) for a change in a color of the thermoebromic material.

14. The method of claim 13, wherein step (iii) further comprises the step of (v) comparing the color to a color chart.

15. The method of claim 12, wherein step (iv) comprises removing the restrictor.

16. The method of claim 12, wherein step (iv) comprises re-sizing the restrictor.

17. The restrictor of claim 7, wherein the band is adjustable.

* * * * *